(12) United States Patent
Hu et al.

(10) Patent No.: US 8,349,299 B2
(45) Date of Patent: Jan. 8, 2013

(54) CONDITIONING AGENT AND A METHOD FOR MAKING HAIR HAVING A SHAPE MEMORY EFFECT

(75) Inventors: Jinlian Hu, Hong Kong (CN); Yong Zhu, Hong Kong (CN); Shaojun Chen, Hong Kong (CN); Hongsheng Luo, Hong Kong (CN); Jing Lu, Hong Kong (CN)

(73) Assignee: The Hong Kong Polytechnic University, Hong Kong (CN)

( * ) Notice: Subject to any disclaimer, the term of this patent is extended or adjusted under 35 U.S.C. 154(b) by 457 days.

(21) Appl. No.: 12/430,904

(22) Filed: Apr. 28, 2009

(65) Prior Publication Data

US 2009/0311210 A1 Dec. 17, 2009

(51) Int. Cl.
*A61Q 5/06* (2006.01)
*A61Q 5/12* (2006.01)

(52) U.S. Cl. .................. 424/70.11; 132/211

(58) Field of Classification Search ........................ None
See application file for complete search history.

(56) References Cited

U.S. PATENT DOCUMENTS

| 6,613,314 | B1 | 9/2003 | Rollat et al. |
| 2002/0197229 | A1 | 12/2002 | Bernard et al. |
| 2008/0311050 | A1* | 12/2008 | Lendlein et al. ............... 424/45 |

FOREIGN PATENT DOCUMENTS

CN 1818198 A 8/2006

OTHER PUBLICATIONS

International Search Report under Patent Cooperation Treaty (PCT) for PCT/CN2008/071310; dated Mar. 26, 2009 ; 3 pages.

* cited by examiner

*Primary Examiner* — Jyothsna Venkat
(74) *Attorney, Agent, or Firm* — Duane Morris LLP; Siegfried J. W. Ruppert

(57) ABSTRACT

A method of imparting a shape memory effect to hair may include administrating an effective amount of a hair-conditioning agent to hair. The hair-conditioning agent may include a shape memory polymer selected from the group consisting of a polyurethane, an acrylic acid copolymer, a pyridine-based copolymer, and a pyrrolidone copolymer.

18 Claims, 2 Drawing Sheets

US 8,349,299 B2

CONDITIONING AGENT AND A METHOD FOR MAKING HAIR HAVING A SHAPE MEMORY EFFECT

BACKGROUND

Traditionally in hairstyle applications, hair-conditioning agents in the form of hair setting liquids, aerosol and non-aerosol sprays, and hair styling foams and gels have been used. While polymers may serve hair setting and thermal insulating functions in the existing conditioning agents, these polymers may be easily washed off, and thus greatly diminish their setting properties.

Shape memory materials have drawn wide attention because of their ability to recover their original shapes upon exposure to an external stimulus. Shape memory materials can find applications in sensors, actuators, smart devices, and media recorders. Examples of shape memory materials may include shape memory alloys, shape memory ceramics, and shape memory polymers.

Traditional shape memory polymers use elastic polymer networks that are equipped with stimuli-sensitive switches. The driving force for shape recovery in these shape memory polymers has usually been the elastic strain that is generated by deformation or by raising the surrounding temperature above the response temperature of the polymers. Deformation at high temperature may be easier to achieve due to the low rubbery modulus of the polymers that may make the orientation of the polymer more feasible. However, the orientation may become partly relaxed before the structure can be frozen during subsequent cooling cycles. On the other hand, deformation at low temperature is difficult due to the high glassy state modulus of the polymers. Shape memory polymers as applied in conditioning agents have been not satisfactorily carried out.

Consequently, it is desirable to have an improved method of applying hair-conditioning agent to impart a shape memory effect to hair. It is also desirable to have the improved hair-conditioning agent such that a hairstyle is more lasting, is retrievable to the set hairstyle when the hairstyle is altered, and the agent is easily removable when finished. It is further desirable to characterize the shape memory effect in hair in two dimensions and three dimensions.

BRIEF SUMMARY

According to another aspect, a method of imparting a shape memory effect to hair may include administrating an effective amount of a hair-conditioning agent to hair. The hair-conditioning agent may include a shape memory polymer selected from the group consisting of a polyurethane, an acrylic acid copolymer, a pyridine-based copolymer, and a pyrrolidone copolymer.

DETAILED DESCRIPTION

Figure 1:
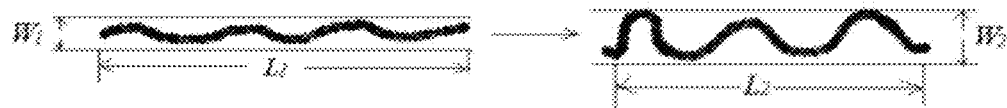
FIG. 1 depicts a schematic of the length and the effective traverse width of a string of hair.

Reference will now be made in detail to a particular embodiment of the invention, examples of which are also provided in the following description. Exemplary embodiments of the invention are described in detail, although it will be apparent to those skilled in the relevant art that some features that are not particularly important to an understanding of the invention may not be shown for the sake of clarity.

Furthermore, it should be understood that the invention is not limited to the precise embodiments described below, and that various changes and modifications thereof may be effected by one skilled in the art without departing from the spirit or scope of the invention. For example, elements and/or features of different illustrative embodiments may be combined with each other and/or substituted for each other within the scope of this disclosure and appended claims. In addition, improvements and modifications which may become apparent to persons of ordinary skill in the art after reading this disclosure, the drawings, and the appended claims are deemed within the spirit and scope of the present invention.

Shape Memory Polymer Network

A shape memory polymer network may include at least one polymer, a plurality of proton accepting heterocyclic groups, a plurality of proton donating groups, and a plurality of cross-link moieties. At least one of the proton accepting heterocyclic groups and the proton donating groups is attached to the at least one polymer.

The proton accepting heterocyclic groups of the network may include at least one pyridine moiety. The pyridine moieties may be formed from a pyridine selecting from the group consisting of ABT-089, abiraterone, 4-aminopyridine, 3,4-diaminopyridine, anabasine, bipyridines, clopyralid, collidine, dianicline, difenpiramide, epibatidine, esomeprazole, fusaric acid, GTS-21, gapicomine, 3-hydroxy picolinic acid, imidacloprid, iproniazid, isoniazid, isonicotinamide, isonicotinic acid, ispronicline, lansoprazole, lercanidipine, linopirdine, 2,6-lutidine, mepyramine, methapyrilene, methylpyridine, milrinone, niacin, nialamide, niceritrol, nicofuranose, nicorandil, nicotinamide, nicotine, nicotinyl alcohol, niflumic acid, nikethamide, nitenpyram, N-nitrosonornicotine, orellanine, picotamide, pirbuterol, pirisudanol, polypyridine complexes, protionamide, pyridoxal, pyridoxamine, pyriproxyfen, pyritinol, quinolinic acid, risedronic acid, rivanicline, rosiglitazone, SCH-530348, sulfapyridine, sulfasalazine, sulfur trioxide pyridine complex, taranabant, tebanicline, triclopyr, and derivatives thereof.

If the pyridine moieties are attached to the polymer of the network, they may be connected to the side chains of the polymer, and/or they may be part of the main chain of the polymer. The pyridine moiety may be connected to an intermolecular chain of the polymer. The polymer may be formed by polymerizing monomers that include a pyridine moiety. Examples of monomers containing pyridine moieties include N,N-bis(2-hydroxyethyl) isonicotinamine (BINA); 2,6-bis (hydroxymethyl) pyridine (HMP); 2,6-diaminopyridine; and 2,6-pyridine dicarboxylic acid. Other 2,6- and 2,5-pyridine units known to one of ordinary skill in the art may also be included.

The proton accepting heterocyclic groups may include at least one moiety formed from a heterocycle selected from the group consisting of furan, pyridazine, pyrazine, selenophene, oxazole, indole, imidazole, pyran, pyrimidine, pyrazine, pyrazole, pyrrole, thiopyran, thiophene, tellurophene, and derivatives thereof.

The proton donating groups of the network may act as proton-donors and may provide protons to form hydrogen bonding with the proton accepting heterocyclic groups. The proton donating groups may include at least one group selected from the group consisting of —NH, such as —NH of urethane group; —NH$_2$; —NH$_3$; —NH$_4^+$; phenol; aliphatic alcohol, such as —OH of hydroxyethyl acrylate and —OH of hydroxy-cellulose; carboxylic acid, such as —COOH of polyacrylic acid; and sulfuric acid.

The cross-link moieties of the network may form physical net-points or chemical cross-linking net-points. The term "net-point" means domains of the polymer that relate to the highest thermal transition temperature. The physical net-points may be formed from the group consisting of a phenyl group, a heterocyclic group, a crown ether group, a polar group, and a urethane group. The chemical cross-linking net-points may be formed from the group consisting of a carbon-carbon double bond group, a hydroxyl group, a carboxylic acid group, an isocyanate group, and an acyl halide group. The acyl halide group may include acyl chloride or acyl bromide.

The shape memory polymer network may also include a segment configured to control and adjust the shape changing conditions of the network, and/or to adjust the dissolvability and the mechanical properties of the network. The segment may be attached to the main-chain of the polymer, to the side-chain of the polymer, or to another polymer chain. The segment may be selected from a group consisting of a polyether group, an alkyl chain group, a hydrophobic group, and a hydrophilic group. Other groups known to one of ordinary skill in the art may also be included. The conditions to be controlled or adjusted may include a response temperature, a response concentration of a gas, and a response speed.

In one embodiment, the shape memory polymer may be selected from the group consisting of polyurethane, an acrylic acid copolymer, a pyridine-based copolymer, and a pyrrolidone copolymer. A solvent may be included in the polymer. The solvent for the polymer may be selected from volatility organic solvent group including of an alkane, an organic acid, an alcohol, an ester, an ether, an ester, and an ketone. The alkane may include methane, ethane, propane, n-butane, isobutane; The acid may include an lactic acid, an acetic acid, a formic acid, an citric acid. The alcohol may include an methanol, an ethanol, and an propanol. The ester may include an ethyl acetate, an ethyl formate, an ethyl lactate, an butyl butyrate, and an ethyl butyrate. Other volatile solvents with a low biological toxicity known to one of ordinary skill in the art may also be used.

The shape memory polymer may have a memory function, and may be used in hair conditioning. The modulus of the polymer at room temperature may range from 1.0 GPa to 5.0 GPa. The memory recovery temperature of the polymer may be adjustable between 40 to 85° C. The polymer may have a shape retentivity of more than 90%, and a recovery rate of more than 85%.

The solvent in the agent may be evaporated by the hair dryer with a hot wind, or a fast wind, or volatilization by itself at ambient condition In one example, the polymer may include polyurethane. The polyurethane may include a functional polyol group (A), a diisocyanate group (B), and a sealant group (C). For example, the polymer may have a C-B-A-B-C structure. Optionally, the polymer may include a chain-extending group (D). For example, the polymer may have a C-B-D-B-A-B-D-B-C structure. Other structures known to one of ordinary skill in the art may also be included.

The difunctional polyol group may be selected from the group consisting of polyoxypropylene polyol, polyoxyethylene polyol, polytetramethylene ether glycol, polyoxypropylene-polyoxyethylene copolyether, hydrolysis resistant polyester polyol, and combinations thereof. The average functionality of the functional polyol may range from 2.0 to 4.0, and the molecular weight may range from 300 to 8000 g/mol. Preferably, the average functionality of the functional polyol may range from 2.0 to 3.0, and the molecular weight may range from 1000 to 6000 g/mol. The term "average functionality" means the average number of active groups in a molecular chain.

The diisocyanate group may include an aromatic diisocyanate group, selected from the group consisting of 2,4-toluene diisocyanate; 4,4'-diphenylmethane diisocyanate; para-phenylene diisocyanate; and liquid methylene diphenyl diisocyanate.

The block agent may contain a ureide pyridone group selected from one of the groups below:

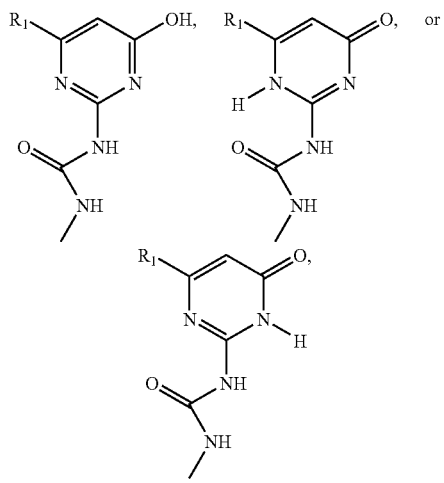

wherein $R_1$ may be a methyl group or an ethylic group.

The chain-extending group may include a difunctional group containing active hydrogen, selected from the group consisting of 1,4-butylene-glycol; 1,6-hexylene glycol; 1,3-propylene-glycol; diethylene glycol; N-methyldiethanol amine; N-ethyl diethanol amine; nicotinic amide; di(hydroxymethyl) benzyl amine; and dimethylol propionic acid.

Method of Making

A method of preparing the shape memory polymer network may include polymerizing monomers containing the proton accepting heterocyclic groups, the proton donating groups, and/or the cross-link moieties using a technique that may include a free radical polymerization method, an ionic polymerization method, a condensation polymerization method, a coordination polymerization method, or an atom transfer radical polymerization method. Conventional processing techniques such as extrusion, injection, blow molding, and laser ablation may be also used to manufacture the polymer network. Other techniques known to one of ordinary skill in the art may also be used.

Hair Conditioning Agent

A hair-conditioning agent may include the shape memory polymer, a solvent, and an auxiliary agent. The auxiliary agent may include an organic diacid such as oxalic acid and polycarboxylic acid such as butanetertracarboxylic acid. The hair-conditioning agent may impart a shape memory effect to hair. The conditioning agent may be in the form of a solution, an emulsion, or a paste.

The hair-conditioning agent may be used alone or as an effective component in a compounded formulation. In one example, the agent may be compounded with 10 weight percent (wt %) of dimethyl polysiloxane, 10 wt % of panthenol, 2.0 wt % of beeswax, and 5.0 wt % of sterin. In another example, the agent may be compounded with 2.0 wt % of castor oil, 5.0 wt % of sterin, 1.2 wt % of carnauba wax, dioctyl maleate, and mineral oil.

Method of Using

A method of imparting a shape memory effect to hair may include administrating an effective amount of a hair-conditioning agent to hair. The hair-conditioning agent may include a shape memory polymer selected from the group consisting of a polyurethane, an acrylic acid copolymer, a pyridine-based copolymer, and a pyrrolidone copolymer; and a solvent.

A method of using the conditioning agent may include spraying or coating the conditioning agent to hair, and then drying the hair. An initial hair configuration, or an initial hairstyle, may be formed upon drying. When the hair temperature is later raised to above the transition temperature of the conditioning agent, the initial hairstyle may be converted into a temporary freeform hairstyle where an external stimulus is applied, assuming a secondary hair configuration. Examples of the external stimuli include heat, moisture, and an external force. When the hair temperature is lowered to the room temperature, and where the external stimulus is maintained, the secondary hair configuration may be set. The secondary hair configuration may recover the initial hairstyle when the temperature of the hair is raised to above the transition temperature.

The transition temperature may be determined using the dynamic mechanic analysis (DMA) measurement. The DMA measurement may measure the modulus change under temperature scan from room temperature to 1° C. The transition temperature is the point when the modulus exhibits a sharp change. For example, 1 gram of hair reagent may be used to make a firm evaporating the solvent, and then to carry out the DMA measurement for the film to confirm the transition temperature.

Method of Characterizing

The shape memory effect on hair may be characterized in one dimension, two dimensions and three dimensions.

Where the shape memory effect of hair is characterized in one dimension, the change of hairstyles may be embodied by the change of the radial length of hair. Where the shape memory effect of hair is characterized in two dimensions and three dimensions, the change of the hairstyles is embodied by the change of the thickness of the hair layer.

While not being bound by theory, it is believe that the change of the radial length of hair has a significant influence on the average thickness of the hair layer. In the case of a string of straight or curly hair, the contribution of the change of its radial length to the thickness of the hair layer may be seen in the form of increasing or reducing the effective transverse width of the hair.

The effect of the change of the radial length of a string of hair on the transverse width is depicted in FIG. 1. An original string of hair may be defined to have a length of $L_1$ and an effective transverse width of $W_1$. When the length is changed to $L_2$, the corresponding transverse width may be changed to $W_2$. While not being bound of theory, it is believed that the parameters may satisfy the following empirical equation:

$$W_2 = W_1 + P \times \left(\frac{L_1 - L_2}{2n_w}\right) \quad (1)$$

wherein $n_w$ is the number of waves on a string of hair; P represents the crimp of hair. For human hair, $n_w$ may range from between 3 to 15, and P may range from between 0.3 and 0.8.

The thickness of a hair layer means the average distance between the surfaces of the hair layers and the head for a certain hairstyle. In the method for characterizing the shape memory effect of hair in two dimensions and three dimensions, the surface of the scalp and the surface of the hair layer may be regarded as part of a circle or sphere, respectively. The thickness of the hair layer may be regarded as the difference between the radii of the circle or sphere corresponding to the surfaces of the hair layer and the scalp.

In characterizing the memory effect of the hair in two dimensions and three dimensions, the radii of the sector and sphere may be measured by the following method: a plastic spherical model having a diameter of 22 cm may be made, and a hair layer of average thickness as found in a human head may be uniformly needle fixed on an outer surface of the spherical model to occupy 30% of the spherical surface.

When the characterizing the memory effect in two dimensions, the radius of a planar image may be measured by making a planar projection of the spherical. When the characterizing the memory effect in three dimensions, the thickness of the hair layer may be determined by selecting 20 to 40 points on the hair layer of the spherical cap, directly measuring the thickness at each point, and calculating the average value.

1-D

The method for characterizing the memory effect of hair in one dimension is as follows: a string of hair having an initial shape after conditioning treatment may be defined to have an initial length of $L_0$. The length $L_0$ may also be regarded as a permanent length of the hair during the shape memory effect. The hair having a length of $L_0$ may be treated with an external stimulus to be converted into a temporary shape. This may be regarded as the shaping treatment of the hair during the shape memory effect. The external stimulus may include a temperature change and an external force. The temperature change may of from about 25 C to 80 C. The external force may include sunlight and moisture. The length of the hair having the temporary shape after subjected to the shaping treatment may be defined to have a temporary length of $L_t$.

The hair having the temporary shape may recover most of the initial shape when the temperature is raised above the transition temperature. This may be regarded as the recovering treatment of the hair during the shape memory effect. This recovery process may also be regarded as a memory process of the initial shape, and is the final state of the memory effect of the treated hair. The length of the hair having most of the initial shape after subjected to the recovering treatment may be defined to have a recovery length of $L_r$.

The overall memory process of hair in one dimension can be expressed as follows:

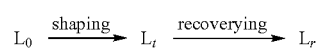

A memory recovery factor in one dimension, $R_1$, in the shape memory process may be defined by the following equation:

$$R_1 = \left(1 - \frac{L_r - L_0}{L_t - L_0}\right) * 100\% \quad (2)$$

In one dimension, $R_1$ of the hair subjected to the hair-conditioning agent may be at least 50%, preferably in the range of from 60% to 80%, and more preferably greater than 80%.

Figure 2:
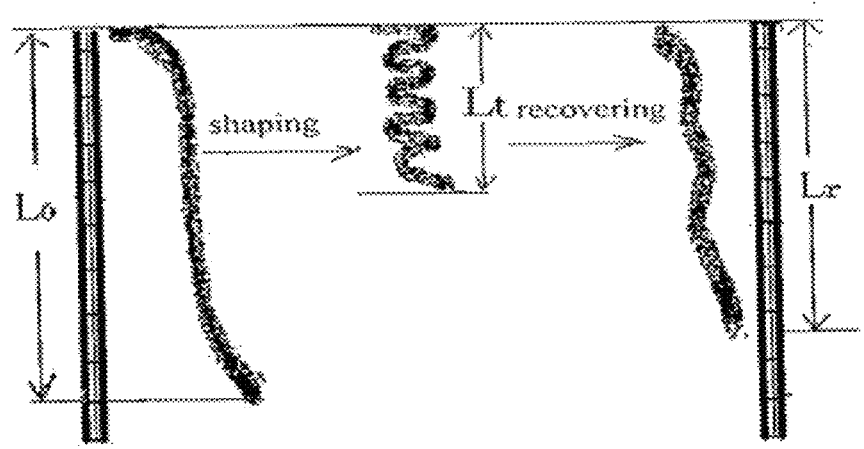
FIG. 2 depicts a diagram of a string of straight hair subjected to a curling treatment and a recovery treatment.

When $L_0$ is greater than $L_t$, the shaping treatment may be regarded as a curling treatment to the hair. The curled hair may have a shape memory effect, and may recover its original length when the temperature of the hair raised. A schematic diagram is shown in FIG. 2.

Figure 3:
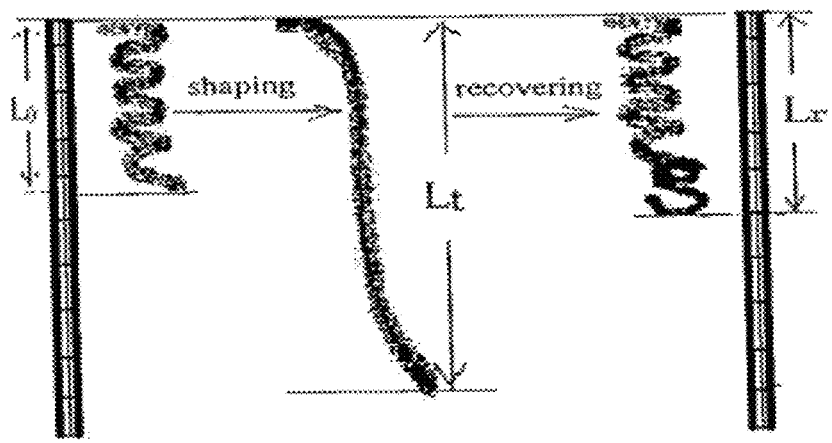
FIG. 3 depicts a diagram of a string of curly hair subjected to a straightening treatment and a recovery treatment.

When $L_0$ is less than $L_t$, the shaping treatment may be regarded as a stretching treatment to the hair. The stretched hair may have a shape memory effect, and may recover its original length when the temperature of the hair is raised to the transition temperature. A schematic diagram is shown in FIG. 3.

2-D

Figure 4:
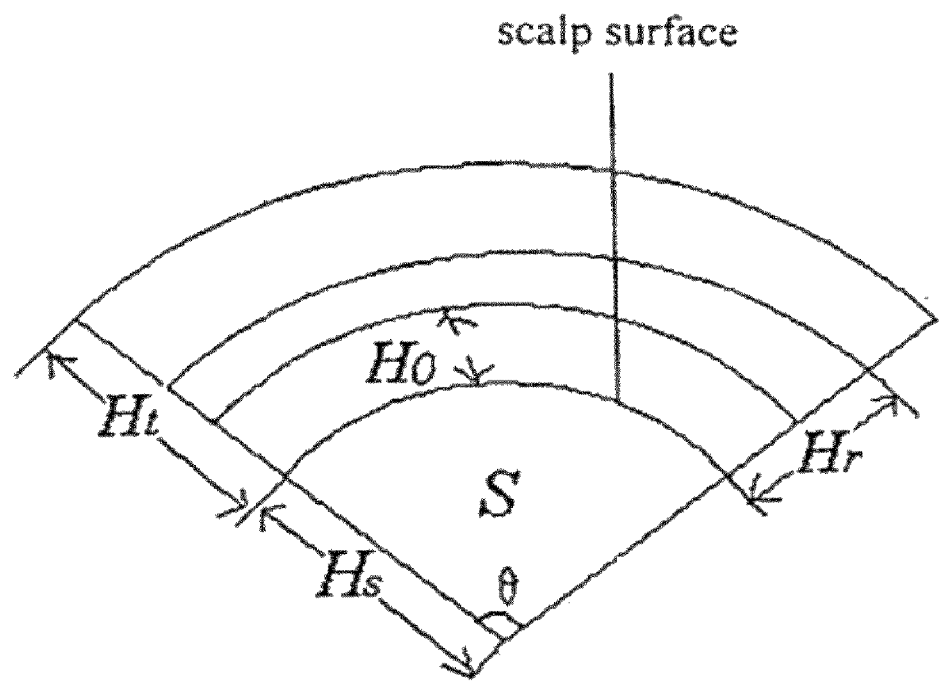
FIG. 4 depicts a diagram of a method for characterizing the memory effect of a string of hair in two dimensions.

A method for characterizing the memory effect of hair in two dimensions is depicted in FIG. 4. The S sector of radius $H_s$ may represent the head surface. The length $H_o$ may represent the average thickness of the hair layer of the initial shape. The length $H_t$ may represent the average thickness of the hair of the temporary shape upon exposure to an external stimulus. The length $H_r$ may represent the average thickness of the hair of the recovered shape after memory recovery upon exposure to another external stimulus.

A memory recovery factor in two dimensions, $R_2$, in the shape memory process may be defined by the following equation:

$$R_2 = \left[1 - \frac{(H_r + H_0 + 2H_s)(H_r - H_0)}{(H_t + H_0 + 2H_s)(H_t - H_0)}\right] \times 100\% \quad (3)$$

Similar to one dimension, when $H_0$ is greater than $H_t$, the shaping treatment may be regarded as a curling treatment to the hair. The curled hair may have a shape memory effect, and may recover its original length when the temperature of the hair is raised. When $H_0$ is less than $H_t$, the shaping treatment may be regarded as a stretching treatment to the hair. The stretched hair may have a shape memory effect, and may recover its original length when the temperature of the hair is raised.

In two dimensions, $R_2$ of the hair subjected to the hair-conditioning agent may be at least 40%, preferably in the range of from 50% to 70%, and more preferably greater than 80%.

3-D

Figure 5:
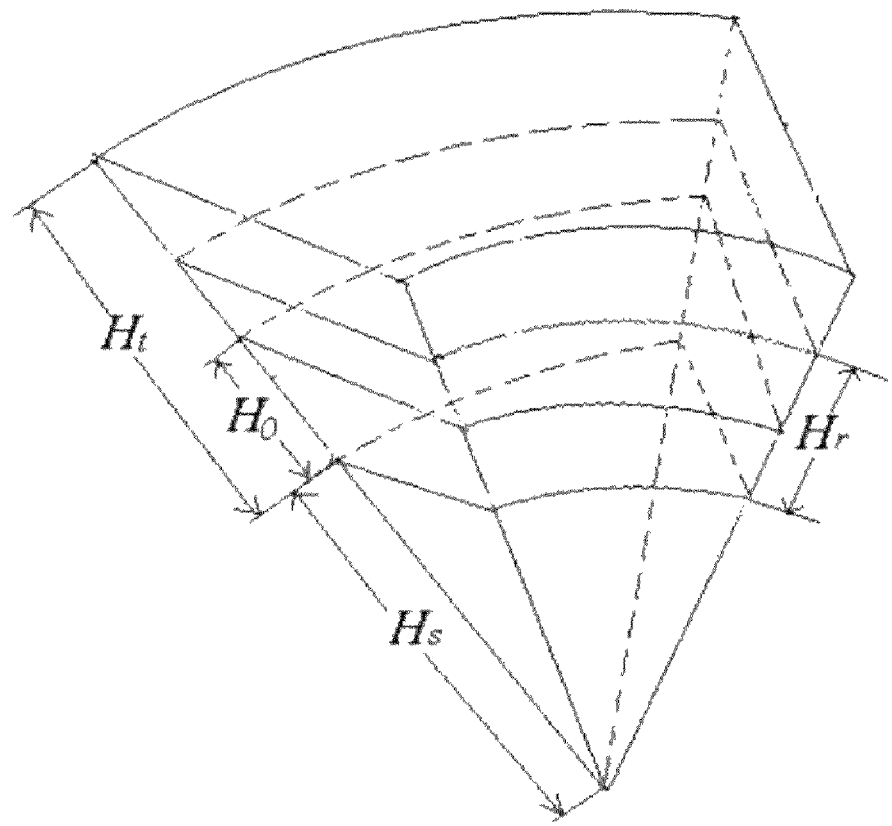
FIG. 5 depicts a diagram of a method for characterizing the memory effect of a string of hair in three dimensions.

A method for characterizing the memory effect of hair in three dimensions is depicted in FIG. 5. Similar to that of two dimensions, the conical space of length $H_s$ may represent the head surface. The length $H_o$ may represent the average thickness of the hair layer in the initial shape. The length $H_t$ may represent the average thickness of the hair layer in the temporary shape upon exposure to an external stimulus. The length $H_r$ may represent the average thickness of the hair layer in the recovered shape after memory recovery upon exposure to another external stimulus.

A memory recovery factor in three dimensions, $R_3$, in the shape memory process may be defined by the following equation:

$$R_3 = \left[1 - \frac{(H_r + H_s)^3 - (H_0 + H_s)^3}{(H_t + H_s)^3 - (H_0 + H_s)^3}\right] \times 100\% \quad (4)$$

When $H_0$ is greater than $H_t$, the shaping treatment may be regarded as a curling treatment to the hair. The curled hair may have a shape memory effect, and may recover its original length when the temperature of the hair is raised. When $H_0$ is less than $H_t$, the shaping treatment may be regarded as a stretching treatment to the hair. The stretched hair may have a shape memory effect, and may recover its original length when the temperature of the hair is raised. In three dimensions, $R_3$ of the hair subjected to the hair-conditioning agent may be at least 30%, preferably in the range of from 40% to 70%, and more preferably greater than 70%.

Having described embodiments of the hair-conditioning agent and method with reference to the accompanying drawings, it is to be understood that the present agent and method are not limited to the precise embodiments, and that various changes and modifications may be effected therein by one having ordinary skill in the art without departing from the scope or spirit as defined in the appended claims.

Furthermore, it should be understood that the agent and method are not limited to the precise embodiments described below and that various changes and modifications thereof may be effected by one skilled in the art without departing from the spirit or scope of the invention. For example, elements and/or features of different illustrative embodiments may be combined with each other and/or substituted for each other within the scope of this disclosure and appended claims.

EXAMPLES

Example 1

Preparation of Shape Memory Polyurethane in Acetic Acid

The pyridine-based shape memory polyurethane (SPMU) was prepared using dimethylfumarate (DMF) as the solvent. The mixture was maintained in an oven at 100° C. for about 24 hours, and then at 80° C. vacuum of about 2 mm Hg for one week to remove the DMF. 5 grams of SMPU was dissolved in 30 grams of acetic acid (AC), then 20 grams of ethanol was charged. A homogeneous SMPU/AC mixture was obtained with even stirring. The resultant SMPU had a transition temperature of 65° C., a shape retentivity of 99%, a shape recovery rate of 90%, a modulus at room temperature of 3 GPa, and a yield strength of about 45 MPa.

Example 2

Preparation of SPMU Hair-Conditioning Agent

The SMPU/AC mixture as prepared in Example 1 was compounded with 10 wt % of dimethyl polysiloxane, 10 wt % of panthenol, 2.0 wt % of beeswax, and 5.0 wt % of sterin. The obtained formulation was used for conditioning Merino wool. The memory recovery factor $R_1$ was measured to be 55%.

Example 3

Memory Recovery Effect of a String of Straight Hair Measured in 1-D

The hair-conditioning agent of Example 2 was applied to the surface of a string of naturally straight hair, and the hair was dried at room temperature. The hair was then wound around a hair curler, and was heated with a hairdryer for 30 seconds. Then, the hair was taken off from the curler to obtain a temporary curly shape. The hair was again heated with the hairdryer, and the hair curls gradually disappeared and recovered the original straight shape. The memory recovery $R_1$ was calculated to be 82%.

Example 4

Memory Recovery Effect of Hair Measured in 2-D

The hair of a human head model having a straight hair layer thickness of 2 cm was treated in the same manner as in Examples 3. The average thickness of the hair layer was measured, and the memory recovery $R_2$ was calculated to be 60%.

Example 5

Memory Recovery Effect of Hair Measured in 3-D

The hair of a human head model having a straight hair layer thickness of 2 cm was treated in the same manner as in Example 3. The average thickness of the hair layer was measured, and the memory recovery $R_3$ was calculated to be 57%.

Example 6

Preparation of Shape Memory Polymer 360 grams of polyoxyethylene glycol ($M_w$ of 3000 g/mol) was reacted with 20.4 grams of 4,4'-diphenylmethane diisocyanate at 80° C. for around 2 hours. Then, 26.4 grams of (2(6-isocyanatohexyl aminocarbonyl-amino)-6-methyl-4 [1H]pyrimidinone ($M_w$ of 293.33 g/mol) was added, and about 2 grams of stannous octoate was added dropwise to react for another 2 hours at 80° C. 400 grams of deionized water and 400 grams of ethanol were added and then cooled to prepare 1206.8 grams of polymer mixture (33.7% of polymer solution). The mixture assumed the state of an opacified and translucent emulsion. The mixture was sampled and was diluted with water or ethanol to adjust the volatility and rheology.

Example 7

Preparation of Hair-Conditioning Agent

The polymer as prepared in Example 6 was compounded with 2.0 wt % of castor oil, 5.0 wt % of sterin, 1.2 wt % of carnauba wax, dioctyl maleate, and mineral oil. The obtained formulation was used in hair setting. Hair was temporarily curled and set, and then was heated using a hairdryer. The memory recovery factor $R_1$ for the hair was calculated to be up to 87%.

Example 8

Memory Recovery Effect of a Lock of Curly Hair Measured in 1-D

The conditioning agent in Example 6 was sprayed on the surface of a lock of naturally curly hair. When the lock of hair was stretched, which was dried by a hairdryer. The lock of hair obtained a temporary straightened shape. The lock of hair was reheated with the hairdryer, and retrieved the original curly shape. The memory recovery $R_1$ was calculated to be 75%.

Example 9

Memory Recovery Effect of Hair Measured in 2-D

The hair of a human head model having a curly hair layer thickness of 2 cm was treated in the same manner as in Example 6. The average thickness of the hair layer was measured, and the memory recovery $R_2$ was calculated to be 55%.

Example 10

Memory Recovery Effect of Hair Measured in 3-D

The hair of a human head model having a curly hair layer thickness of 3 cm was treated in the same manner as in Example 6. The average thickness of the hair layer was measured, and the memory recovery $R_3$ was calculated to be 47%.

Example 11

Memory Recovery Effect of Merino Wool Measured in 2-D

The wool on a spherical model coated with Merino wool having a hair layer thickness of 3 cm was treated in the same manner as in Example 6. The average thickness of the hair layer obtained by planar projection was measured, and the memory recovery rate $R_2$ was calculated to be 62%.

Example 12

Memory Recovery Effect of Merino Wool Measured in 3-D

The wool on a spherical model coated with Merino wool having a hair layer thickness of 3 cm was treated in the same manner as in Example 6. The average thickness of the hair layer on the periphery of the spherical model was measured, and the memory recovery $R_3$ was calculated to be 55%.

While hair having a shape memory effect has been described, it should be understood that the effect is not so limited, and modifications may be made. The scope of the effect is defined by the appended claims, and all devices that come within the meaning of the claims, either literally or by equivalence, are intended to be embraced therein.

What is claimed is:
1. A method for imparting a shape memory effect to hair, comprising the step of:
 administrating an effective amount of a hair-conditioning agent to hair;
  wherein the hair-conditioning agent comprises a shape memory polymer comprising:
  a polyurethane;
  and wherein the polyurethane is formed from
  (i) an oligomer polyol group;
  (ii) a diisocyanate group; and
  (iii) a sealant group selected from the group consisting of

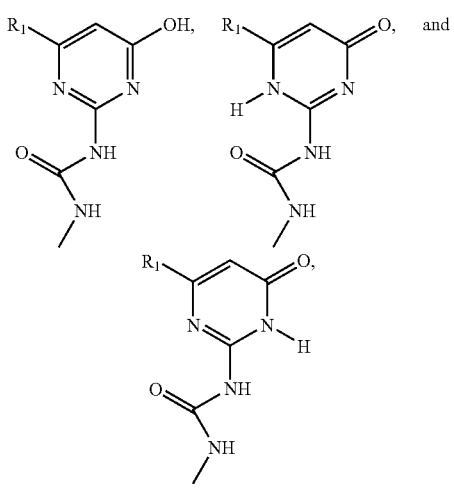

wherein R₁ is a methyl group.

2. The method of claim 1, wherein the step of administrating comprises immersing, coating, or spraying the hair-conditioning agent to hair.

3. The method of claim 1, further comprising the steps of:
raising the temperature of the hair; and
subjecting the hair to an external stimulus.

4. The method of claim 3, wherein the external stimulus comprises heat, moisture, or an external force.

5. The method of claim 3, further comprising the step of:
lowering the temperature of the hair and maintaining the external stimulus.

6. The method of claim 5, further comprising the step of:
raising the temperature of the hair to above a transition temperature.

7. The method of claim 1, wherein the oligomer polyol group is selected from the group consisting of polyoxypropylene polyol, polyoxyethylene polyol, polytetramethylene ether glycol, polyoxypropylene-polyoxyethylene copolyether, hydrolysis resistant polyester polyol, and combinations thereof.

8. The method of claim 1, wherein the diisocyanate group is selected from the group consisting of 2,4-toluene diisocyanate, 4,4'-diphenylmethane diisocyanate, para-phenylene diisocyanate, and methylene diphenyl diisocyanate.

9. The method of claim 1, wherein the shape memory polymer further comprises a chain-extending group.

10. The method of claim 9, wherein the chain-extending group is selected from the group consisting of 1,4-butyleneglycol, 1,6-hexylene glycol, 1,3-propylene-glycol, diethylene glycol, N-methyldiethanol amine, N-ethyl diethanol amine, nicotinic amide, di(hydroxymethyl) benzyl amine, and dimethylol propionic acid.

11. The method of claim 1, wherein the hair-conditioning agent further comprises 10 weight percent (wt%) of dimethyl polysiloxane, 10 wt % of panthenol, 2.0 Wt % of beeswax, and 5.0 wt % of sterin.

12. The method of claim 1, wherein the hair-conditioning agent further comprises 2.0 wt % of castor oil, 5.0 wt % of sterin, 1.2 wt % of carnauba wax, dioctyl maleate, and mineral oil.

13. The method of claim 1, wherein the shape memory polymer further comprises a shape retentivity of more than 90%.

14. The method of claim 1, wherein the shape memory polymer further comprises a memory recovery temperature of between 50° C. to 85° C.

15. The method of claim 1, wherein the shape memory polymer further comprises a modulus at room temperature of from 2.0 GPa to 5.0 GPa.

16. The method of claim 1, wherein the shape memory effect is characterized by a memory recovery factor in one dimension, $R_1$, as defined by the equation below:

$$R_1 = \left(1 - \frac{L_r - L_0}{L_t - L_0}\right) * 100\%$$

wherein $L_o$ represents an initial length of a string of hair, $L_t$ represents a temporary hair length after subjected to a shaping treatment to the hair, and $L_r$ represents a recovery hair length after subjected to a recovering treatment to the hair; and wherein $R_1$ is at least 70%.

17. The method of claim 1, wherein the shape memory effect is characterized by a memory recovery factor in two dimensions, $R_2$, as defined by the equation below:

$$R_2 = \left[1 - \frac{(H_r + H_0 + 2H_s)(H_r - H_0)}{(H_t + H_0 + 2H_s)(H_t - H_0)}\right] \times 100\%$$

wherein $H_o$ represents an average thickness of a hair layer in the initial shape, $L_t$ represents average thickness of the hair layer in the temporary shape upon exposure to an external stimulus, and $L_r$ represents an average thickness of the hair layer in the recovered shape upon exposure to another external stimulus; and wherein $R_2$ is at least 70%.

18. The method of claim 1, wherein the shape memory effect is characterized by a memory recovery factor in three dimensions, $R_3$, as defined by the equation below:

$$R_3 = \left[1 - \frac{(H_r + H_s)^3 - (H_0 + H_s)^3}{(H_t + H_s)^3 - (H_0 + H_s)^3}\right] \times 100\%$$

wherein $H_o$ represents an average thickness of a hair layer in the initial shape, $L_t$ represents average thickness of the hair layer in the temporary shape upon exposure to an external stimulus, and $L_r$ represents an average thickness of the hair layer in the recovered shape upon exposure to another external stimulus; and wherein $R_3$ is at least 70%.

* * * * *